US011426076B2

(12) United States Patent
Pierro

(10) Patent No.: US 11,426,076 B2
(45) Date of Patent: Aug. 30, 2022

(54) CONTACTLESS SYSTEM AND METHOD FOR ASSESSING AND/OR DETERMINING HEMODYNAMIC PARAMETERS AND/OR VITAL SIGNS

(71) Applicant: Vivonics, Inc., Bedford, MA (US)

(72) Inventor: Michele Pierro, Westford, MA (US)

(73) Assignee: Vivonics, Inc., Bedford, MA (US)

(*) Notice: Subject to any disclaimer, the term of this patent is extended or adjusted under 35 U.S.C. 154(b) by 0 days.

(21) Appl. No.: 17/104,230

(22) Filed: Nov. 25, 2020

(65) Prior Publication Data

US 2021/0153744 A1 May 27, 2021

Related U.S. Application Data

(60) Provisional application No. 62/941,072, filed on Nov. 27, 2019.

(51) Int. Cl.
*A61B 5/024* (2006.01)
*A61B 5/00* (2006.01)
(Continued)

(52) U.S. Cl.
CPC .......... *A61B 5/0075* (2013.01); *A61B 5/0059* (2013.01); *A61B 5/0064* (2013.01); (Continued)

(58) Field of Classification Search
CPC ... A61B 5/0075; A61B 5/0064; A61B 5/0059; A61B 5/0077; A61B 5/02405; (Continued)

(56) References Cited

U.S. PATENT DOCUMENTS 7,183,549 B2 2/2007 Teich et al.
8,350,908 B2 1/2013 Morris et al.
(Continued)

FOREIGN PATENT DOCUMENTS

EP 3052008 B1 8/2017

OTHER PUBLICATIONS

Ali Al-Naji et al. "Remote monitoring of cardiorespiratory signals from a hovering unmanned aerial vehicle." BioMed Eng Online (2017) 16:101.*

(Continued)

*Primary Examiner* — Amanda Lauritzen Moher
(74) *Attorney, Agent, or Firm* — Iandiorio Teska & Coleman, LLP

(57) ABSTRACT

A contactless system for assessing and/or determining hemodynamic parameters and/or vital signs is featured. The system includes one or more contactless light sources configured to emit light incident on a moving living subject at one more wavelengths absorbed by one or more chromophores associated with spontaneous hemodynamic oscillations in a predetermined area of the living subject. The system includes a camera subsystem including one or more cameras configured to receive reflected light from the predetermined area of the moving living subject and configured to track motion of the predetermined area of the living subject within a field of view of the camera subsystem and configured to generate a time sequence of images of the predetermined area of the living subject. A controller is coupled the one or more light sources and the camera subsystem and is configured to acquire the time sequence of images and configured to generate one or more non-contact PPG waveforms and to assess and/or and determine one or hemodynamic parameters and/or vital signs from the one or more non-contact PPG waveforms. One or more polarizers (Continued)

are preferably each coupled to one of the one or more light sources are preferably configured to polarize the light to a polarized state such that the polarized light in the polarized state diffuses into the tissue in the predetermined area at a predetermined depth range and the polarized light is maintained in the polarized state at the predetermined depth range. A detector polarizer is preferably coupled to each of the one or more cameras and is configured to discriminate the light maintained in the polarized state and at the predetermined depth range and configured to generate the time sequence of images of the predetermined area with improved signal quality of the resulting non-contact PPG waveform.

22 Claims, 14 Drawing Sheets

(51) Int. Cl.
A61B 5/11 (2006.01)
A61B 5/145 (2006.01)
A61B 5/08 (2006.01)
G16H 30/40 (2018.01)

(52) U.S. Cl.
CPC ........ *A61B 5/0077* (2013.01); *A61B 5/02405* (2013.01); *A61B 5/08* (2013.01); *A61B 5/1122* (2013.01); *A61B 5/14542* (2013.01); *A61B 5/6801* (2013.01); *A61B 5/6887* (2013.01); *G16H 30/40* (2018.01); *A61B 2576/00* (2013.01); *G06T 2207/10016* (2013.01)

(58) Field of Classification Search
CPC . A61B 5/1122; A61B 5/14542; A61B 5/6801; A61B 5/6887; A61B 5/08; A61B 2576/00; G16H 30/40; G06T 2207/10016
See application file for complete search history.

(56) References Cited

U.S. PATENT DOCUMENTS

| | | |
|---|---|---|
| 8,913,791 B2 | 12/2014 | Datta et al. |
| 9,165,375 B2 | 10/2015 | Datta et al. |
| 9,749,526 B2 | 8/2017 | Chuang et al. |
| 9,962,090 B2 | 5/2018 | DiMaio et al. |
| 10,448,835 B2* | 10/2019 | Pierro ................ A61B 5/02405 |
| 2013/0342670 A1* | 12/2013 | Kyal ..................... A61B 5/7225 348/77 |
| 2015/0031965 A1* | 1/2015 | Visvanathan ........ A61B 5/0205 600/301 |
| 2015/0145950 A1 | 5/2015 | Murphy et al. |
| 2017/0202463 A1 | 7/2017 | Muhlsteff et al. |
| 2017/0367580 A1 | 12/2017 | DiMaio et al. |
| 2018/0235487 A1* | 8/2018 | Paul ....................... A61B 5/352 |
| 2018/0325397 A1* | 11/2018 | Presura ............... A61B 5/0535 |
| 2019/0223730 A1 | 7/2019 | Pierro et al. |
| 2019/0286233 A1* | 9/2019 | Newberry ............... G06F 1/169 |
| 2019/0350471 A1 | 11/2019 | Marks et al. |
| 2020/0053342 A1 | 2/2020 | Macmillan et al. |
| 2021/0153744 A1 | 5/2021 | Pierro |

OTHER PUBLICATIONS

Kumar et al. "DistancePPG: Robust non-contact vital signs monitoring using a camera." Biomedical Optics Express 6(5): 1565-1588, 2015.*

G de Haan et al. "Improved motion robustness of remote-PPG by using the blood volume pulse signature." Physiol. Meas. 35: 1913-1926, 2014.*

Maeda et al. "Comparison of Measurement Sites and Light Sources in Photoplethysmography during Walking." Biomedical Engineering 49(1): 132-138, 2011.*

English translation of Meada's "Comparison of Measurement Sites and Light Sources in Photoplethysmography during Walking" (Biomedical Engineering 49(1): 132-138, 2011). Google Translate, accessed May 27, 2022.*

Abuella et al., "Non-Contact Vital Signs Monitoring Through Light Sensing", IEEE Sensors Journal, Nov. 10, 2019, pp. 1-12.

Hu et al., "Feasibility of Imaging Photoplethysmography", 2008 International Conference on BioMedical Engineering and Informatics, IEEE 2008, pp. 72-75.

Sun et al., "Noncontact Monitoring of Vital Signs with RGB and Infrared Camera and Its Application to Screening of Potential Infection", Chapter 4, IntechOpen, 2018, pp. 43-51.

Van Gastel et al., "Motion Robust Remote-PPG In Infrared", IEEE Transactions on Biomedical Engineering, vol. 62, No. 5, May 2015, pp. 1425-1433.

Van der Kooij et al., "An Open-Source Remote Heart Rate Imaging Method With Practical Apparatus and Algorithms", Behavior Research Methods (2019) 51, pp. 2106-2119.

Written Opinion of the International Application No. PCT/US20/62154, dated Aug. 20, 2021, (nine (9) pages).

* cited by examiner

CONTACTLESS SYSTEM AND METHOD FOR ASSESSING AND/OR DETERMINING HEMODYNAMIC PARAMETERS AND/OR VITAL SIGNS

RELATED APPLICATIONS

This application claims benefit of and priority to U.S. Provisional Application Ser. No. 62/941,072 filed Nov. 27, 2019, under 35 U.S.C. §§ 119, 120, 363, 365, and 37 C.F.R. § 1.55 and § 1.78, which is incorporated herein by this reference.

GOVERNMENT RIGHTS

This invention was made with U.S. Government support under Contract No. W81XH-17-C-0169, awarded by the U.S. Army. The Government has certain rights in the invention.

FIELD OF THE INVENTION

This invention relates to a contactless system and method for assessing and/or determining hemodynamic parameters and/or vital signs of one or more living subjects,

BACKGROUND OF THE INVENTION

Conventional systems and methods to determine hemodynamic parameters and/or vital signs of one or more living subjects, e.g., the heart rate, the resting heart rate, the heart rate variability, the respiration rate, the oxygen saturation, and the like, of one or more living subjects typically require direct contact of sensors (which for optical sensors includes the light sources and the detectors) of the system with the skin of a living subject. Therefore, such conventional systems and methods may be considered intrusive to some living subjects. Direct contact of the sensors of such conventional systems and methods may also interfere with the comfort of the living subjects which may result in some living subjects feeling anxious and/or nervous. Such negative experiences may alter the heart rate and respiration rate which may result in inaccurate results to healthcare providers or any person who may desire to monitor the hemodynamic parameters and/or vital signs of living subjects. The direct contact of the sensors may also lead to skin irritations.

Thus, significant attention is currently focused on the research and development of technology that can provide contactless measurements of hemodynamic parameters and/or vital signs of living subjects. Several such systems are based on acquisition of the photoplethysmography (PPG) signal, which detects changes in the blood volume at a sensed location.

One conventional contactless system and method for remote measurement of vital signs is disclosed is U.S. Pub. No. 2019/0350471 to Marks et al., incorporated by reference herein. Marks et al. teaches sensitivity of a remote PPG (M) signal to noise in the measurements of intensities of the skin of a human subject is caused in part by independent derivations of PPG waveforms from the intensities of the skin measured at different spatial positions. Marks et al. teaches a complex and cumbersome process that relies on reducing noise by replacing an independent estimation with a joint estimation of different PPG waveforms of intensity of a skin at different regions of the skin using a solver in the frequency domain to determine frequency coefficients that correspond to a person's vital signs using an iterative process.

U.S. Pat. No. 10,448,835 by the Assignee hereof teaches a contactless system and method for assessing tissue viability and other hemodynamic parameters. However, the '835 Patent, which is, principally intended to detect locations of viable versus necrotic tissues, similarly relies on complex and cumbersome frequency and time domain analysis and also relies on using a complex two-dimensional hemodynamic map. The '835 Patent also teaches the human subject is required to be in a stationary position in order to acquire the necessary data/signals.

Other conventional non-contactless systems that use a light source, a detector, and creating PPG waveforms are known. See e.g., *Feasibility of Imaging Photoplethysmography* by Hu et al.; an *Open-Source Remote Heart Rate Imaging Method With Practical Apparatus and Algorithms* by van derr Kooif; European Patent Application No. 3052008; and U.S. Patent Publication No. 2017/0367580, all incorporated by reference herein. However, such conventional systems teach the subject is in a stationary or fixed position.

*Motion Robust Remote-PPG in Infrared* by van Gastel et al. teaches improving motion robustness of a cardiac pulse using a complex method of selecting a specific light spectrum with dedicated LEDs. However, van Gastel et al. teaches nothing related to tracking the motion of a moving living subject, e.g., humans or animals.

Thus, there is a need for a less complex and accurate contactless system and method for assessing and/or determining hemodynamic parameters and/or vital signs of one or more living subjects that are moving.

SUMMARY OF THE INVENTION

In one aspect, a contactless system for assessing and determining hemodynamic parameters and/or vital signs is featured. The system includes one or more contactless light sources configured to emit light incident on a moving living subject at one more wavelengths absorbed by one or more chromophores associated with spontaneous hemodynamic oscillations in a predetermined area of the living subject. The system includes a contactless camera subsystem including one or more cameras configured to receive reflected light from the predetermined area of the living subject and configured to track motion of the predetermined area of the moving living subject within a field of view of the camera subsystem and configured to generate a time sequence of images of the predetermined area of the living subject A controller is coupled to the camera subsystem and is configured to acquire the time sequence of images and configured to generate one or more non-contact PPG waveforms and to assess and/or and determine one or more hemodynamic parameters and/or vital signs from the one or more non-contact PPG waveforms. One or more polarizers are preferably each coupled to one of the one or more contactless light sources and are preferably configured to polarize the emitted light to a polarized state such that the polarized light in the polarized state diffuses into tissue in the predetermined area at a predetermined depth range and the polarized light is maintained in the polarized state at the predetermined depth range. A detector polarizer is preferably coupled to each of the one or more cameras and is configured to discriminate the light maintained in the polarized state and at the predetermined depth range and configured to generate the time sequence of images of the predetermined area with improved signal quality of the resulting non-contact PPG waveform.

In one embodiment, the controller may be further configured to perform one or more of: a) acquire the time sequence of images, b) select a region of interest in an image of the time sequence of images at a predetermined point in time, c) process the pixels in a region of interest in the image to generate a single value representative of an intensity of the reflected light from the predetermined area and generate a sample, d) repeat steps b) and c) for one or more images in the acquired time sequence of images to generate a time sequence of samples, and e) generate the non-contact PPG waveform from the time sequence of samples The one or more contactless light sources may be configured to emit light having wavelengths in the visible, near infra-red or infra-red range. The predetermined area of the living subject may include any area of the living subject having exposed skin. The hemodynamic parameters and/or vital signs may include one or more of: a heart rate, a resting heart rate, a heart rate variability, a respiration rate, and an oxygen saturation of the living subject. The one or more cameras may include one or more CCD cameras, one or more CMOS cameras, or one or more thermal imaging cameras. The one or more cameras may include an array of photodiodes or an array of phototransistors. The region of interest may be selected based on the range of intensity of the reflected light in that region across the time sequence of images. The region of interest in each image may be selected to correspond to the same portion of the predetermined area for each image of the sequence of images. The one or more of the cameras may be configured to move relative to the living subject. The one or more cameras may be a moveable camera that may be hand-held, body-worn, mounted on a drone, mounted on a vehicle, mounted on a wheeled dolly, or mounted on rails. The field of view may include a composite field of view comprised of a field of view from two or more cameras, a wide field of view from a single camera, or one or more moving field of views from one or more moving cameras.

In another aspect, a method for assessing and determining hemodynamic parameters and/or vital signs is featured. The method includes contactlessly emitting light incident on a moving living subject at one or more wavelengths absorbed by one or more chromophores associated with spontaneous hemodynamic oscillations in a predetermined area of the moving living subject. The method also includes tracking motion of the predetermined area of the moving living subject within a field of view and generating a time sequence of images of the predetermined area. The method also includes acquiring the time sequence of images, generating one or more non-contact PPG waveforms and assessing and/or determining one or more hemodynamic parameters and/or vital signs from the one or more non-contact PPG waveforms. The method also preferably includes polarizing the light incident on the living subject to a polarized state such that the polarized light in the polarized state diffuses into the tissue in the predetermined area at a predetermined depth range and the polarized light is maintained in the polarized state at the polarized depth. The method also preferably includes discriminating the light maintained in the polarized state and at the predetermined depth range and generating the time sequence of images of the predetermined area with improved signal quality of the resulting non-contact PPG waveform.

In one embodiment, the method may further include performing one or more of: a) acquiring a time sequence of images, b) selecting a region of interest in an image of the time sequence of images at a predetermined time, c) processing the pixels in a region of interest in the image to generate a single value representative of an intensity of reflected light from predetermined area and generating a sample, d) repeating steps b) and c) for each one or more images in the acquired time sequence of images to generate a plurality of time sequence of samples, and e) generating the non-contact PPG waveform from the time sequence of sample. The light incident on the living subject may be emitted having wavelengths in the visible, infrared, or near-infrared range. The predetermined area of the living subject may include any area of the living subject having exposed skin. The hemodynamic parameters and/or vital signs may include one or more of: a heart rate, a resting heart rate, a heart rate variability, a respiration rate, and an oxygen saturation of the living subject. The region of interest may be selected based on the range of intensity of the reflected light in that region across the time sequence of images. The region of interest in each image may be selected to correspond to the same portion of the predetermined area for each image of the sequence of images. Tracking motion of the predetermined area of the living subject within the field of view may be performed by a camera subsystem comprising one or more cameras configured to move relative to the living subject. The one or more cameras may be a moveable camera that may be hand-held, body-worn, mounted on a drone, mounted on a vehicle, mounted on a wheeled dolly, or mounted on rails. The field of view may include a composite field of view comprised of a field of view from two or more cameras, a wide field of view from a single camera, or one or more moving fields of views from one or more cameras.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 9 is a block diagram showing an example of additional steps which may be performed by the method shown in. FIG. 8 to contactlessly assess and/or determining hemodynamic parameters and/or vital signs.

DETAILED DESCRIPTION OF THE INVENTION

Figure 1A:
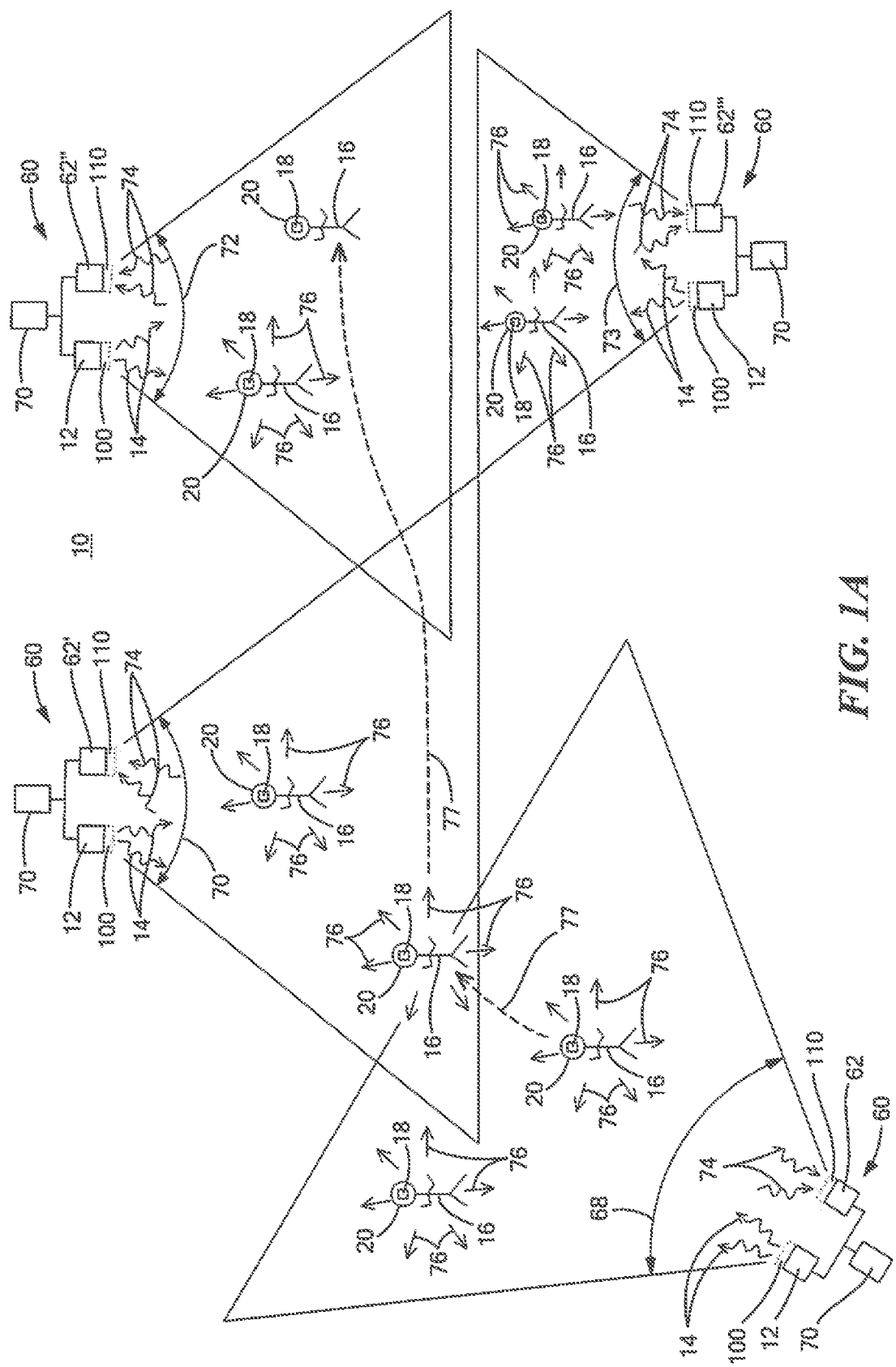
FIG. 1A is a schematic diagram showing the primary components of one example of the contactless system and method for assessing and/or determining hemodynamic parameters and/or vital signs using a camera subsystem including multiple cameras to define a composite field of view (FOV)

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

The blood vessels throughout the body can be categorized as arteries, veins and capillaries. These different compartments feature differences in the manner in which the volume of blood flows through each type of blood vessel. Blood flow volume through veins changes little, whereas blood flow volume through arteries varies according to the pulse. Additionally, one of the properties of oxygenated hemoglobin present in both venous and arterial blood is that oxygenated hemoglobin absorbs light within a broad spectrum of wavelengths. Thus, if the skin of a predetermined area of a living subject is exposed to continuous light, the reflected light changes according to variation in blood flow volume, and the pulse waveform can be obtained by continuing to measure that reflected light, thus creating a waveform herein called non-contact photoplethysmography (PPG) waveform, as discussed in detail below.

Figure 1B:
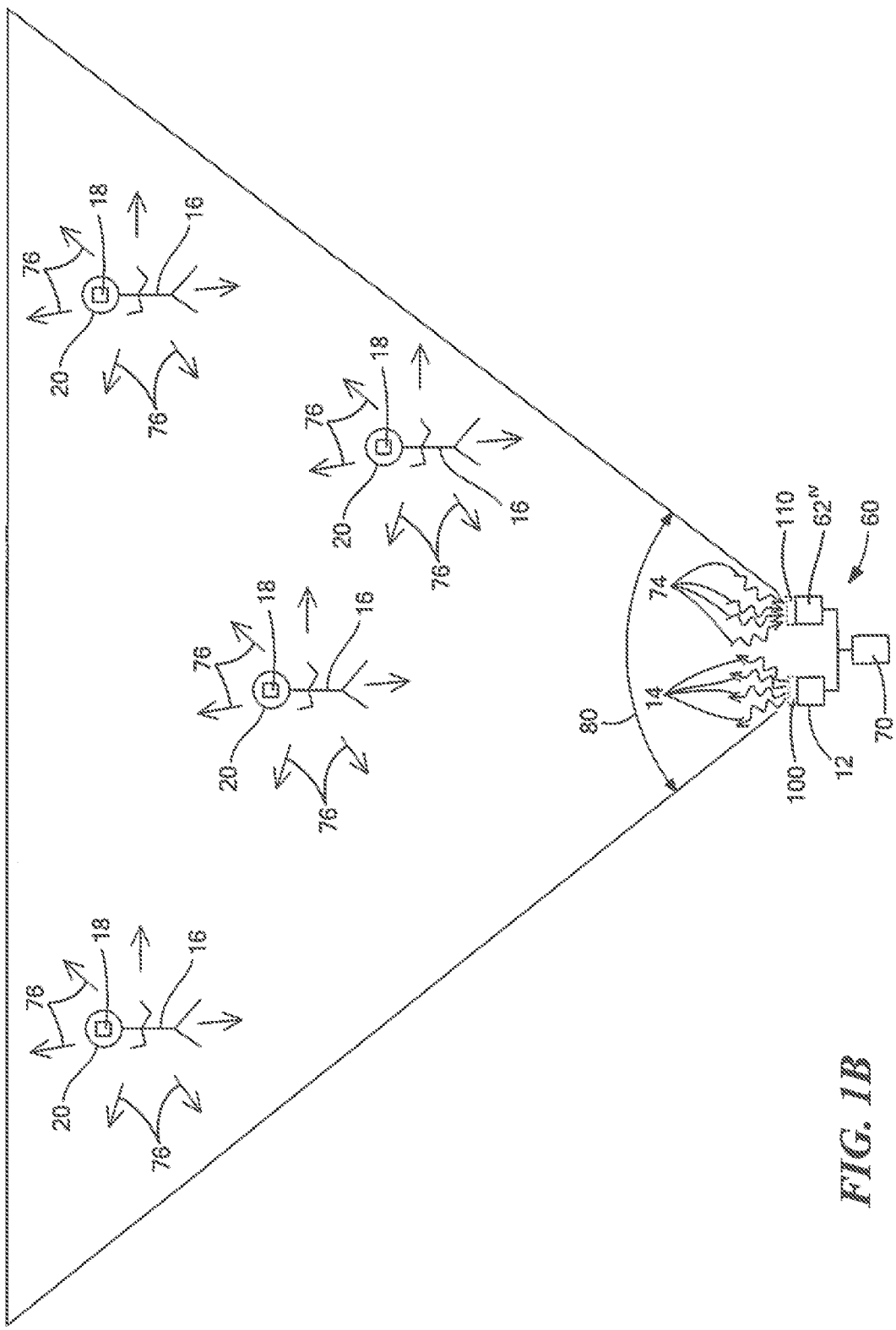
FIG. 1B is a schematic diagram showing the primary components of one example of the contactless system and method for assessing and/or determining hemodynamic parameters and/or vital signs using a camera subsystem including a single camera having a wide FOV.
Figure 1C:
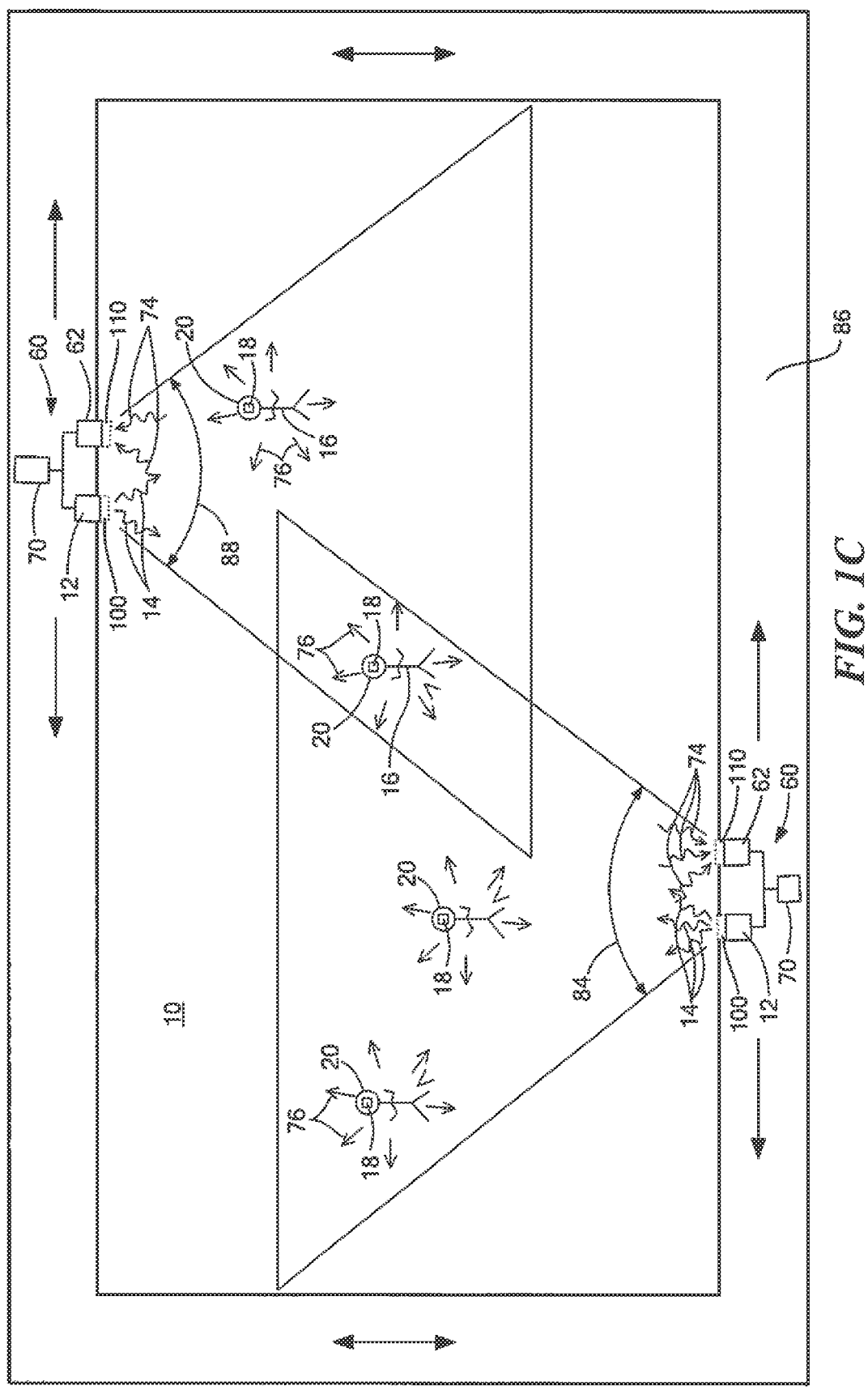
FIG. 1C is a schematic diagram showing the primary components of one example of the contactless system and method for assessing and/or determining hemodynamic parameters and/or vital signs using a movable camera subsystem.

Contactless system 10, FIGS. 1A, 1B, 1C, and 2 for assessing and/or determining hemodynamic parameters and/or vital signs includes one or more contactless light sources 12 configured to emit light 14 incident on moving living subject 16 at one more wavelengths absorbed by one or more chromophores associated with spontaneous hemodynamic oscillations in predetermined area 18 of living subject 16. In one design, one or more contactless light sources 12 may preferably include any type of light source or an array of light sources which emit(s) light having wavelengths in the visible, near infrared, or infrared range, e.g., in the range of about 400 nm to about 1,000,000 nm. In another design, one or more contactless light sources 12 may specifically include near infrared (NIR) light sources, such as light emitting diodes or laser diodes, and/or any type of light source which emits light having wavelengths in the near infrared range, e.g., in the range of about 700 am to about 3,000 am, In this example, predetermined area 18 is preferably an exposed area of exposed skin located on face 20 of living subject 16 as shown. In other examples, predetermined area 18 may be any area of exposed area of skin located on living subject 16, e.g., any area of head 22, FIG. 2, or any area of: ear 24, chest 28, back 30, arm 32 or arm 34, hand 36 or hand 38, any of fingers 40 or fingers 42, leg 44 or leg 46, foot 48 or foot 50, toes 52 or toes 54, or any desired exposed area of living subject 16. One or more contactless light sources 12 FIGS. 1A-1C are located such that they do not contact predetermined area 18 of living subject 16. Living subject 16 may be a human living subject as shown or an animal.

System 10 also includes contactless camera subsystem 60 comprising one or more cameras. In the example show in FIG. 1A, camera subsystem 60 preferably includes cameras 62, 62', 62" and 64'". Each of cameras 62, 62', 62" and 64'" have a field of view (FOV), FOV 68 for camera 62, FOV 70 for camera 62', FOV 72 for camera 62", and FOV 73 for camera 62'". Each of cameras 62, 62', 62" and 62'" or receive reflected light 74 from predetermined area 18 of living subject 16 within their FOV as shown. Camera subsystem 60 tracks motion of the predetermined area 18 of living subject 16 within the field of view of the camera subsystem and generates time sequence of images 94, FIG. 3, of predetermined area 18 of living subject 16. In this example, the FOV of camera subsystem 60, FIG. 1A, is preferably a composite FOV comprised of the area covered by the combination of FOV 68, FOV 70, FOV 72, and FOV 73. Thus, camera subsystem 60 tracks motion of predetermined area 18 of living subject 16 within each of FOV 68, FOV 70, FOV 72, and FOV 73, e.g., as shown by arrows 76, or tracks motion of predetermined area 18 of living subject 16 from one FOV to another, e.g., from FOV 68 to FOV 70 to FOV 72, as shown by arrows 77. Camera subsystem 60 may include any number of cameras such that the FOV of each camera can be combined to provide full coverage of tracking motion of predetermined area 18 of one or more living subjects 16 within a predetermined environment, e.g., a hospital, a stadium, an airport, a train station, a gym, a room, or any type of facility.

In another example, the FOV provided by camera subsystem 60 may be a wide FOV with an angle that covers a large area, e.g., from 0° to about 360°, from a single camera, e.g., camera $62^{IV}$, FIG. 1B, with wide FOV 80.

In yet another example, camera subsystem 60 may include one or more moveable cameras that track motion of the predetermined area of the living subject, e.g., movable camera 62, FIG. 1C, with FOV 84 mounted on rails 86 or moveable camera 62' with FOV 88 mounted on rails 86. In other designs, camera subsystem 60 may include a moveable camera that is hand-held, body-worn, mounted on a drone, mounted on a vehicle, mounted on a wheeled dolly, or similar movement device with a FOV that tracks motion of predetermined area 18 of living subject 16.

One or more contactless light sources 12, FIGS. 1A-1C may be in a fixed location to preferably emit light 14 the covers the FOV of all of one or more cameras 62, 62', 62", 62''' and 64$^{IV}$ discussed above in all of their orientations. In some examples, emitted light 14, FIGS. 1A-1C, may be part of an ambient light source in the environment and one or more contactless light sources 12 discussed supra and infra may not necessarily be utilized.

One or more cameras 62, 62', 62", 62''', and 62$^{IV}$, FIGS. 1A-1C, may be a charged coupled device (CCD) camera, a complementary metal-oxide semiconductor (CMOS) camera, a thermal imaging camera, an array of photodiodes or phototransistors, or similar type device as known by those skilled in the art.

Camera subsystem 60 may utilize the systems and/or methods disclosed in one more of U.S. Pat. No. 8,350,908 for Tracking People and Objects Using Multiple Live and Recorded Surveillance Camera Videos, U.S. Pat. No 8,913,791 for Automatically Determining Field of View Overlap Among Multiple Cameras, and/or U.S. Pub. No. 2015/0145950 for Multi Field-Of-View Multi Sensor Electro-Optical Fusion-Zoom Camera, ail incorporated by reference herein, or similar type device known to those skilled in the art, and modify camera subsystem 60 including one or more cameras 62, 62', 62", 62''' and 64$^{IV}$ to receive reflected 74 light from predetermined area 18 associated with spontaneous hemodynamic oscillations of moving living subject 16 within a field of view of the camera subsystem as discussed above and in further detail below.

Thus, contactless camera subsystem 60 effectively and efficiently tracks motion of predetermined area 18 associated with spontaneous hemodynamic oscillations of living subject 16. Camera subsystem 60 may utilize a composite FOV, a wide FOV, or move to follow and track the predetermined area 18 when living subject 16 moves. If the movement of living subject 16 is minimal, controller 70 preferably adjusts the region of interest (discussed in detail below) from frame to frame in sequence of images 94, FIG. 3, and continues to detect arid track at the same desired predetermined area 18 of living subject 16.

Figure 4A:
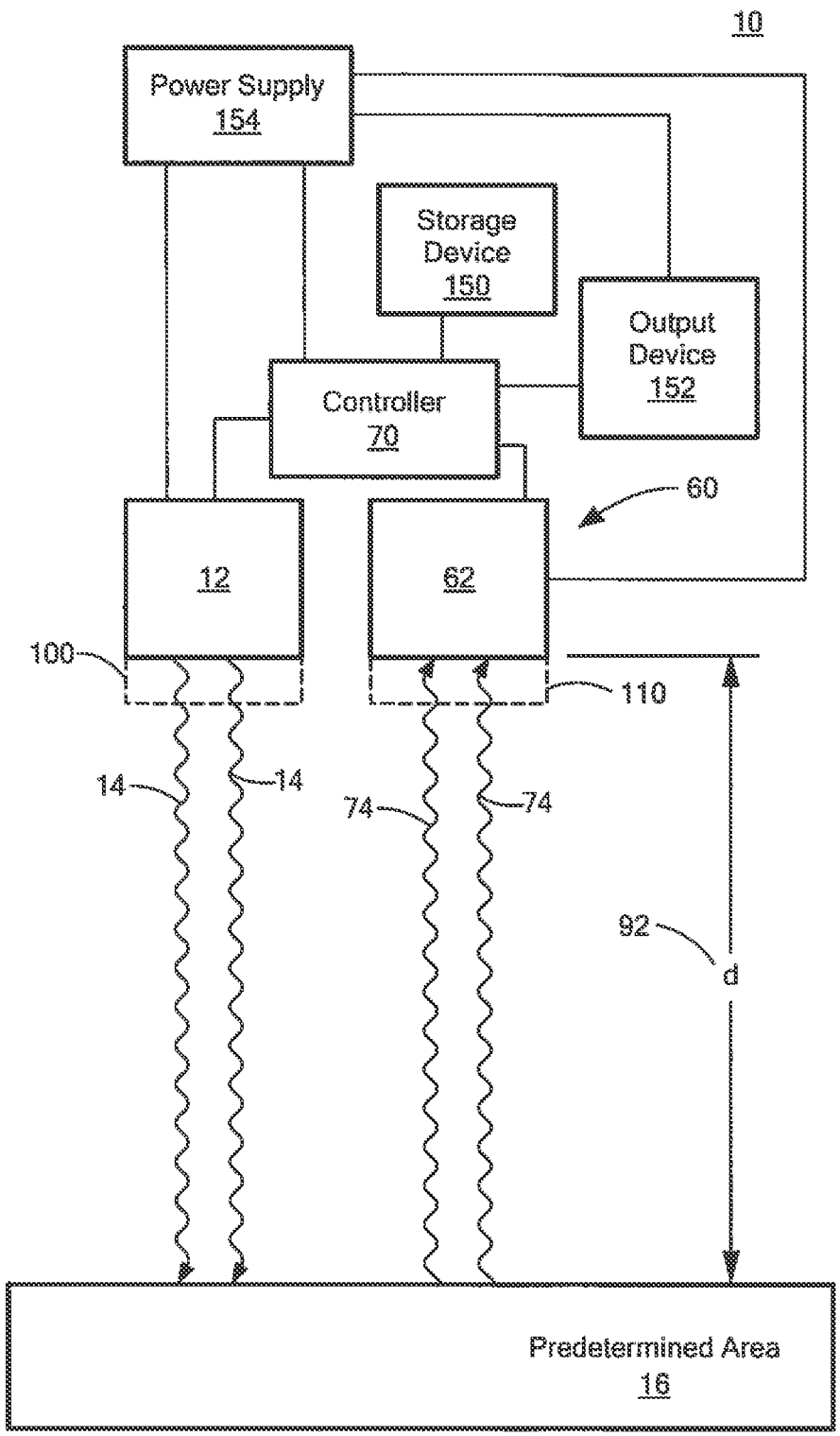
FIG. 4A is a schematic diagram showing in further detail the primary components of the system shown in one or more of FIGS. 1-3 for an example when the one or more contactless light sources and the one or more cameras are located in close proximity to each other.

In one design, one or more of contactless light sources 12, FIGS. 1A 1C, and one of more of cameras 62, 62', 62", 64''' or 64$^{IV}$ may be located in close proximity to each other, e.g., as shown in FIG. 4A, because the light 14 emitted from one or more contactless light sources 12 to one or more cameras 62 is nearly parallel to the reflected light 74 from the predetermined area 18 of living subject 16 to one or more cameras 62. Additionally, because light 14 emitted by one or more contactless light sources 12 may experience scattering, e.g., as shown by scattered light 74' FIG. 4B, one or more contactless light sources 12 and one or more cameras 62 may be separated from each other such that they are not in close proximity to each other as shown.

Figure 2:
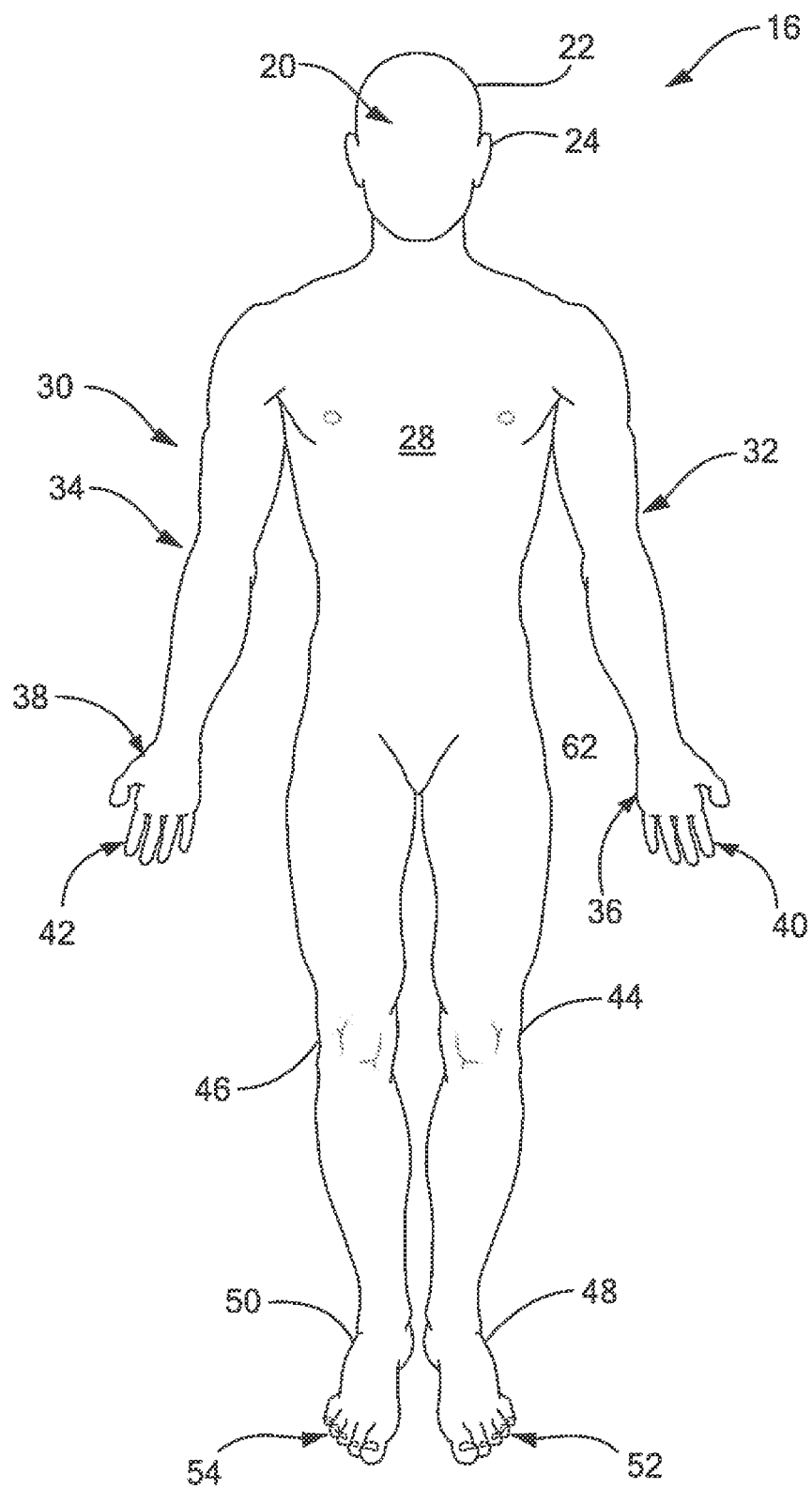
FIG. 2 is a schematic diagram showing examples of different locations of the predetermined area shown in FIGS. 1A-1C on a human subject.
Figure 3:
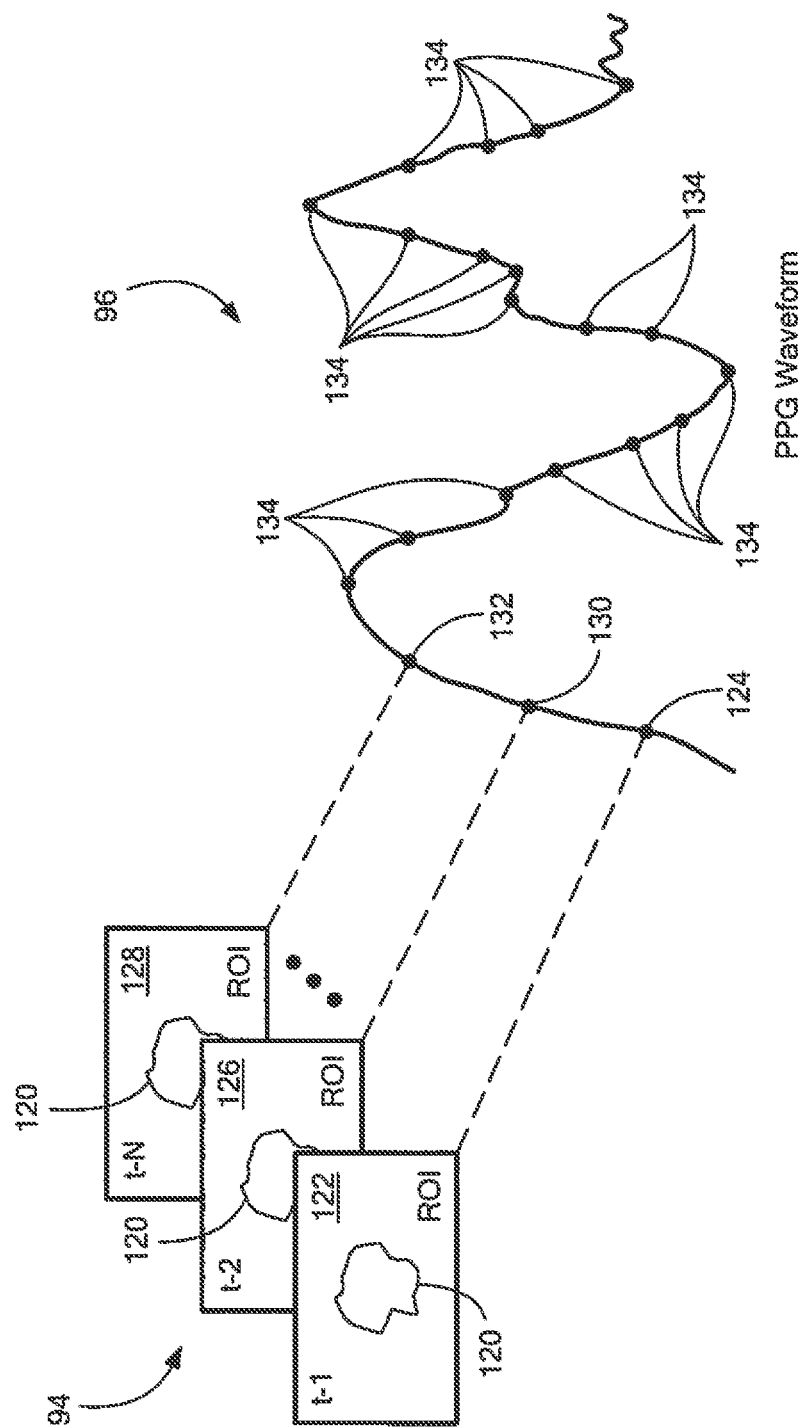
FIG. 3 shows an example of the time sequence of images and the non-contact photoplethysmography (PPG) generated by the system shown in FIGS. 1A-1C and FIG. 2.
Figure 4B:
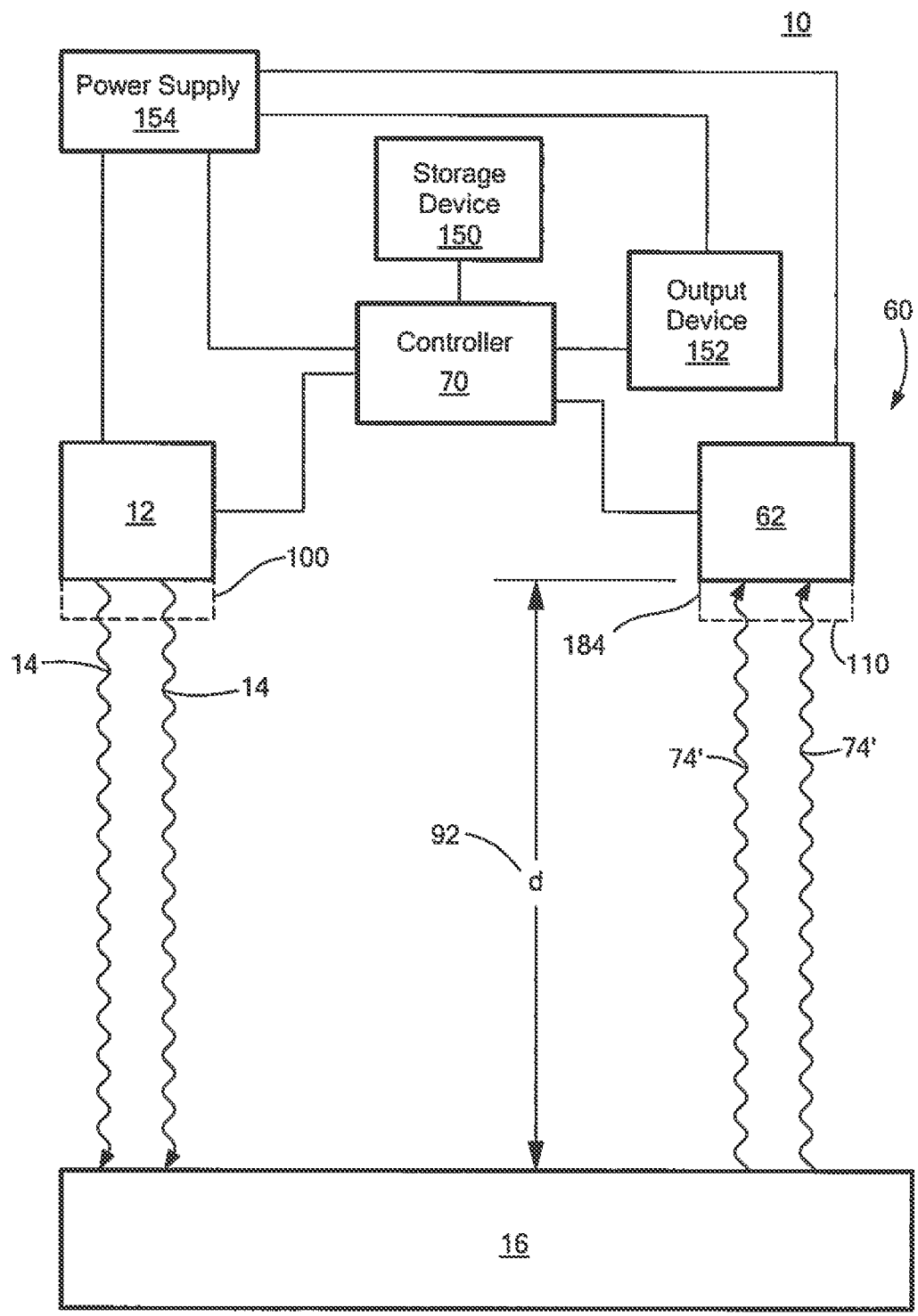
FIG. 4B is a schematic diagram showing in further detail the primary components of the system shown in one or more of FIGS. 1-3 for an example when the one or more contactless light sources and the one or more cameras shown are spaced apart from each other for subject/s' hemodynamic parameters remote monitoring.

Camera subsystem 60 shown in one or more of FIGS. 1A-4B is preferably located a predetermined desired distance from predetermined area 18 of living subject 16, exemplarily shown by predetermined desired distance d-92, FIGS. 4A and 4B. In one example, the predetermined desired distance d-92 may be from about 1 mm to any desired maximum distance, e.g., about 1 m, about 2 m, about 10 m, or similar longer or shorter distances, where the maximum distance of one or more cameras 62 of camera subsystem 60 from predetermined area 18 of living subject 16 preferably depends on the intensity of emitted light 14, FIGS. 1A-1C and 4A 4B, and reflected light 74, or scattered light 74' and the sensitivity and resolution of one or more cameras 62. As discussed below, this feature allows for system 10 to assess and/or determine hemodynamic parameters and/or vital signs of living subjects which may be located a far distance from system 10, e.g., in a hospital setting to assess and/or determine hemodynamic parameters and/or vital signs of patients or to assess and/or determine hemodynamic parameters and/or vital signs of a large population of living subjects, e.g., at airports, train stations, stadiums, airports, gyms, or any type of facility.

System 10 also includes controller 70, FIGS. 1A-1C, and 4A-4B, coupled to one or more contactless light sources 12 and camera subsystem 60. Controller 70 acquires time sequence of images 94, FIG. 3, and generates one or more non-contact PPG waveforms, e.g., non-contact PPG waveforms 96, as discussed in further detail below, to assess and/or and determine one or more hemodynamic parameters and/or vital signs from the one or more non-contact PPG waveforms. Details of determining one or more hemodynamic parameters and/or vital signs from non-contact PPG waveform 96 are disclosed in e.g., Sun et al., *Noncontact Monitoring of Vital Signs with RGB and Infrared Camera and Its Application to Screen of Potential Infection*, Chapter 4, IntechOpen, 2018 and Abuella et al., *Non-contact Vital signs Monitoring through Light Sensing*, IEEE Sensors Journal, Vol. X, No. X, 10 Nov. 2019, both incorporated by reference herein, and similar techniques as known by those skilled in the art.

In one example, the hemodynamic parameters and/or vital signs assessed and determined by system 10 preferably include one or more of: heart rate, resting heart rate, heart rate viability, respiration rate and breathing pattern, and oxygen saturation of living subject 16. Other hemodynamic parameters and/or vital signs known by those skilled in the art may also be assessed and determined.

Figure 5A:
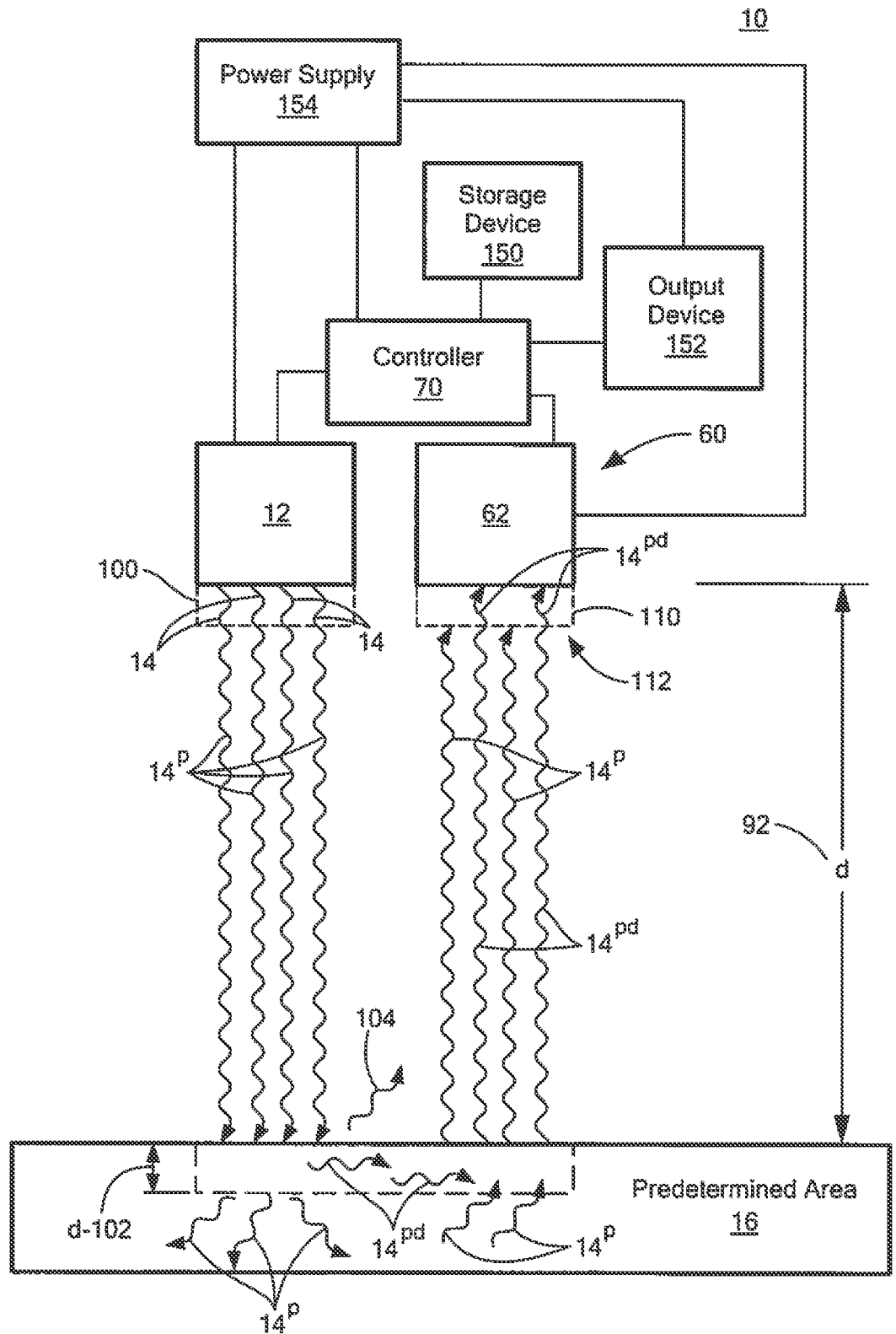
FIG. 5A is a schematic diagram showing in further detail one example of polarizers coupled to the one or more contactless light sources and detector polarizers coupled to one or more cameras for the example shown in FIG. 4A.
Figure 5B:
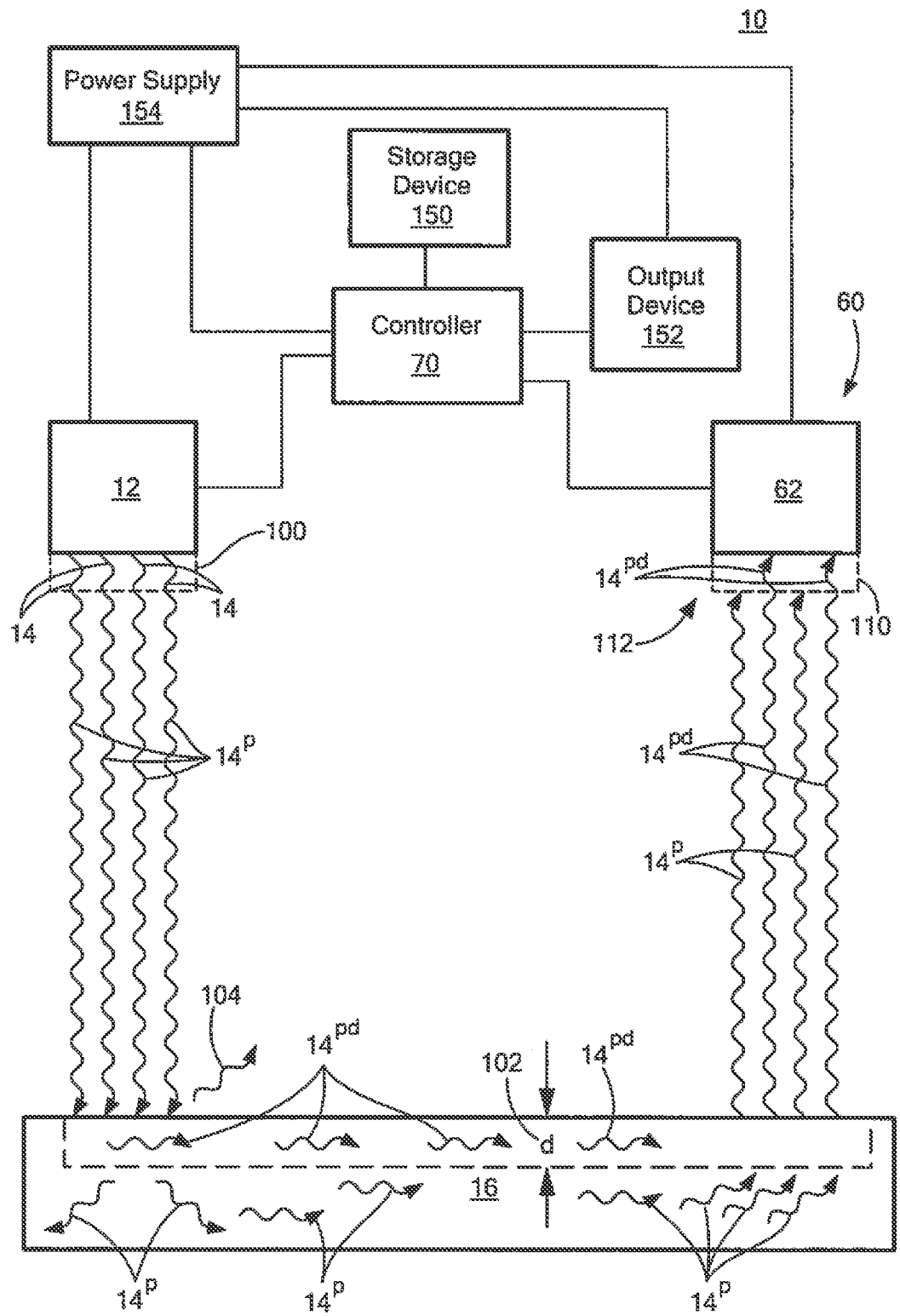
FIG. 5B is a schematic diagram showing in further detail one example of polarizers coupled to the one or more contactless light sources and detector polarizers coupled to one or more cameras for the example shown in FIG. 4B.

System 10 also preferably includes one or more polarizers 100, FIGS. 1A-1C and 4A-4B, each coupled to one or more contactless light sources 12 as shown. FIG. 5A shows in further detail an example of polarizer 100 coupled to contactless light source 12 for the example shown in FIG. 4A and FIG. 5B shows in further detail one example of polarizer 100 coupled to light source 12 for the example shown in FIG. 4B. Each of the one or more contactless light sources 12 shown in FIGS. 1A-1C preferably includes polarizer 100 coupled thereto as shown. Each polarizer 100 coupled to light source 12 polarizes emitted light 14 to polarized state 14$^P$ such that polarized light 14$^P$ in the polarized state diffuses into the tissue in predetermined area 18 of living subject 16 and polarized light 14$^P$ is maintained in the polarized state at a predetermined depth, e.g. predetermined depth d-102. In one example, depth d-102 is preferably in the range of about 0.1 mm to about 0.5 mm. In other examples, depth d-102 may be greater or less than this range. For example, when polarized light 14$^P$ is incident on the tissue in predetermined area 18, some of the photons in polarized light 14$^P$ will reflect off the surface of tissue 16 and some photons will penetrate into the tissue in predetermined area 18 where the photons will either be scattered or absorbed as shown. If light polarized 14$^P$ incident light is reflected off the surface of the tissue of predetermined area 18 of living subject 16, e.g., indicated at 104, the polarization state is perfectly maintained. However, the polarization state of the penetrating photons of polarized light 14$^P$ may be affected by scattering events in tissue of subject 16 which may be divided into two categories: polarization maintaining or depolarized. If the photons do not travel deep into the tissue of predetermined area 18 only a limited number of scattering events will occur and the polarization is maintained, but some alterations have likely occurred. However, if photons travel deeper into the tissue in predetermined area 18 and more scattering events occur, the polarization of polarized light $14^P$ becomes increasingly depolarized. Therefore, by utilizing one or mom polarizer 100 each coupled to one or more contactless light sources 12, the degree of polarization can be maintained to discriminate the depth of penetration of light into the tissue of tissue 16, e.g., polarized light 14 at depth d-102, e.g., about 0.1 mm to about 0.5 min. Such a depth is preferably utilized for real-time assessment and/or and determination of one or hemodynamic parameters and/or vital signs of predetermined area 18 of living subject 16 by clinicians in an objective manner, as discussed below.

Figure 6:
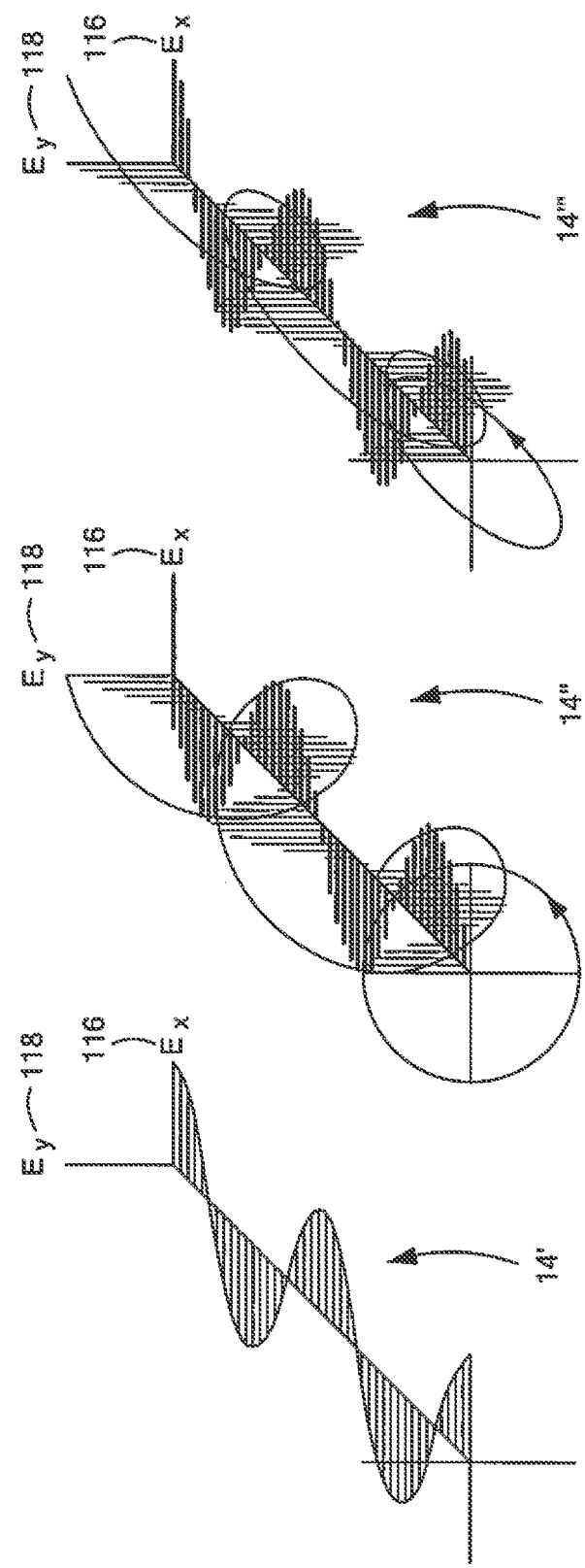
FIG. 6 shows examples of polarized light which may be used for the system shown in one or more of FIGS. 1-5B.

Polarized light $14^P$ emitted from each polarizer 100 may provide a relatively low-cost solution to enable real-time assessment and/or and determination of one or hemodynamic parameters and/or vital signs of predetermined area 18. As polarized light $14^P$ transversely propagates trough time and space, it contains both oscillating orthogonal electric and magnetic field vectors. The polarization of polarized light $14^P$ as disclosed herein refers to the direction and manipulation of the oscillating electric field vector. Polarization may be produced and manipulated by polarizer 100 coupled to one or more contactless light sources 12. Polarizer 100 may be placed in any desired position along path of light 14, shown in one or more of FIGS. 1A-5B, to the tissue in predetermined area 18 of living subject 16. Polarized light $14^P$ provided by one or more contactless light sources 12 and polarizer 100 coupled thereto may include linearly polarized light 14', FIG. 6, circular polarized 14" or elliptical polarized light 14''', depending on the arrangement of the optical components used. Linearly polarized light 14 may be produced when a single electric field oscillation plane is isolated using polarizer 100 configured as linear polarizer, where one oscillation plane is dictated by the polarizing axis. The resulting electric field vector is considered to oscillate in one plane in which the orthogonal Ex-116 and Ey-118 components are maintained the same phase and amplitude as shown. Circularly polarized light 14 may be provided by polarizer 100 coupled to one or more contactless light sources 12 when one of the two Ex-116 and Ey-118 components of the linearly polarized electric field vector becoming out of phase by exactly ±90 from the other as shown. Circularly polarized light 14" may be provided by polarizer 100 coupled to one or more contactless light sources 12 when polarizer 100 is configured as a quarter-wave plate rotated 45 degrees relative to the polarizing axis of the linear polarizer. As circularly polarized light propagates through time, the shape of the propagation may be considered as a helix rotating either clockwise or counter-clockwise, which is denoted as right-handed or left-handed respectively. Elliptically polarized light 14''' is provided by polarizer 100 coupled to one or more contactless light sources 12 when linearly polarized light passing through polarizer 100 is configured as a wave plate or birefringent material where the electric field vector components become out of phase by any amount other than ±90 degrees. Polarized light 14', polarized light 14" or polarized light 14''' provided by polarizer 100 coupled to one or more contactless light sources 12 under these different polarization states will respond differently when focused on a turbid media, such the tissue located in predetermined area 18 shown in one or more of FIGS. 1A-5B of living subject 16.

In the example discussed above with reference to FIGS. 5A and 5B, polarized light $14^p$ and polarized light $14^{pd}$ may be one or more of polarized light 14', 14", and/or 14''', FIG. 3.

System 10 also preferably includes one or more detector polarizers 110, FIGS. 1A-1C, 4A-4B, and 5A-5B, each coupled to one or more cameras 62 62', 62°, 64" and $64^{IV}$. FIG. 5A shows in further detail an example of detector polarizer 110 coupled to camera 62 for the example shown in FIG. 4A and FIG. 5B shows in further detail one example of detector polarizer 110 coupled to camera 62 for the example shown in FIG. 4B. Each of detector polarizers 110 discriminate between polarized light $14^{pd}$ maintained in the polarized state and at the predetermined depth, d-102, from the tissue in predetermined area 18 and polarized light $14^P$ reflected from the tissue in predetermined area 18 which has not been maintained in the polarized state and at the predetermined depth. For example, as shown generally by arrow 112, FIGS. 5A and 5B, each detector polarizer 110 coupled to one or more cameras, in this example cameras 62, discriminates between polarized light $14^{pd}$ that has been maintained in the polarized state at predetermined depth, d-102, in the tissue in predetermined area 18 and polarized light $14^P$ which has not been maintained in the polarized state at predetermined depth, d-102.

Using polarizers 100, FIGS. 1A-1C, 4A-4B, and 5A-5B, and detector polarizers 110 as discussed above provides one or more cameras 62, 62', 62", and 62''' with the ability to generate time sequence of images 94, FIG. 3, of predetermined area 18 with improved signal quality of the resulting non-contact PPG waveform 96, In one embodiment, controller 70, FIGS. 1A-1C, 4A-4B, and FIGS. 5A-5C preferably performs step a) acquiring a time sequence of images, e.g., time sequence of images 94, FIG. 3., of predetermined area 18 of moving living subject 16. Controller 70 also preferably performs step h) selecting a region of interest (ROI) in an image of the time sequence of images at a predetermined point of time, e.g., ROI 120 in image 122 at time t-1. Controller 70 also preferably performs step c) processing the pixels in ROI-120 in image 122 to generate a single value representative of an intensity of reflected light 74, FIGS. 1A-1C and 4A and 4B, or discriminated polarized light $14^{pd}$, FIGS. 5A-5B, that has been maintained in the polarized state at predetermined depth, d-102, and generate a sample, e.g., sample 124. Controller then preferably performs step d) which includes repeating steps b) and c) for one or more images in the acquired time sequence of images 94, e.g., for exemplary image 126 at time t-2 and exemplary image 128 at time t-N to generate a time sequence of samples, e.g., exemplary samples 130 and 132, respectively. In this example, three images from a time sequence of images 122, 126, 128, are shown at times t-1, t-2, and t-N, respectively, and three samples 124, 130, and 132 are created. However, in operation, controller 70 may acquire any desired number of images as needed as known by those skilled in the art to generate a desired number of samples to create PPG waveform 96, e.g., the samples exemplary indicated at 134. Each of samples 124, 130, 132 and 134 preferably correspond to a value calculated from each ROI of each acquired frame. In step c) above, the processing of the pixels in a region of interest (ROI) in the image to generate a single value representative of an intensity of the reflected light from predetermined area may include calculating a sum or an average value of all the pixels in the ROI or calculating a weighted sum or average of the pixels with weights assigned by relative spatial position, for example to weight pixels in the center of the ROI more than those near the edges of the ROI, or calculated a weighted or unweighted sum or average of all the pixels in the ROI that have values above some minimum threshold or values below some maximum threshold or both. Further, the processing of the pixels in a region of interest (ROI) in the image to generate a single value representative of an intensity of the reflected light from the predetermined area may include calculating a sum or average of the values obtained by multiplying the value of each pixel by a scaling factor which is a function of the value of that pixel in order to emphasize or deemphasize pixels of certain values over others. Further, the processing of the pixels in a region of interest (ROI) in the image to generate a single value representative of an intensity of the reflected light from the predetermined area may include calculating a sum or average of the values obtained by multiplying the value of each pixel by a scaling factor based on the values of the pixels in its immediate vicinity to emphasize clusters of pixels within the ROI.

Thus, system 10 and method thereof discussed below uses time domain analysis for generating a single value representative of the intensity of the reflected light from predetermined area 18 of moving living subject 16 and generating samples as discussed above and does not rely on frequency domain analysis or generating a two-dimensional hemodynamic map. Using time domain analysis is less complex and cumbersome than frequency domain analysis and does not rely on using complex two-dimensional hemodynamic maps. Controller 70 may perform one or more or all of steps a), b), c) and d) discussed above.

Controller 70, FIGS. 1A-1C, 4A-4B, and 5A-5B may include one or more processors, an application-specific integrated circuit (ASIC), firmware, hardware, and/or software (including firmware, resident software, micro-code, and the like) or a combination of both hardware and software that may all generally be referred to herein as "controller", which may be part of system 10 and method thereof of this invention. Controller 70 also preferably stores data associated with the time sequence of images 94, FIG. 3, the plurality of samples, non-contact PPG waveform 96, the assessed and/or and determined one or more hemodynamic parameters and/or vital signs of predetermined area 18 of moving living subject 16 created by system 10 discussed above in storage device 150. Storage device 150 may include any combination of computer-readable media or memory. The computer-readable media or memory may be a computers readable signal medium or a computer-readable storage medium. A computer-readable storage medium or memory may be electronic, magnetic, optical, electromagnetic, infrared, or semiconductor system, apparatus, or device, or any suitable combination of the foregoing. Other examples may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. As disclosed herein, the computer-readable storage medium or memory may be any tangible medium that can contain, or store one or more programs for use by or in connection with controller 70.

System 10 also preferably includes output device 152 coupled to controller 70 and configured to output the non-contact PPG waveforms and/or the assessed and determined hemodynamic parameters and/or vital signs, e.g., a display device, such as a computer monitor or screen, a printout from a printer or similar type device, one or more computer files, a stream of data communications, and the like. System 10 also preferably includes power supply 154 preferably configured to provide power to one or more contactless light sources 12, camera subsystem 60, controller 70 and output device 152.

In one design, the ROI, e.g., ROI 120, FIG. 3, is preferably select based on a range of intensities of reflected light in the region across the time sequence of images, e.g., time sequence of image 94. In one example, the ROI, e.g., ROI 120, in each image of time sequence of images 94 may be selected to correspond to the same portion of predetermined area 18, FIGS. 1A-1C, 4A-4B, and 5A-5B of moving living subject 16 for each image in the image of sequence of images 94, FIG. 3. In other examples, the ROI may not necessarily be selected to correspond to the same portion of predetermined area 18 of moving living subject 16 for each image in the image of sequence of images 94, for example, if predetermined are 18 on forehead 20, FIGS. 1A-2 is no longer available, e.g., living subject 16 puts on a hat, processor 70 may be configured to determine another available predetermined area 18 of moving living subject 16 and select a different ROI.

Figure 7:
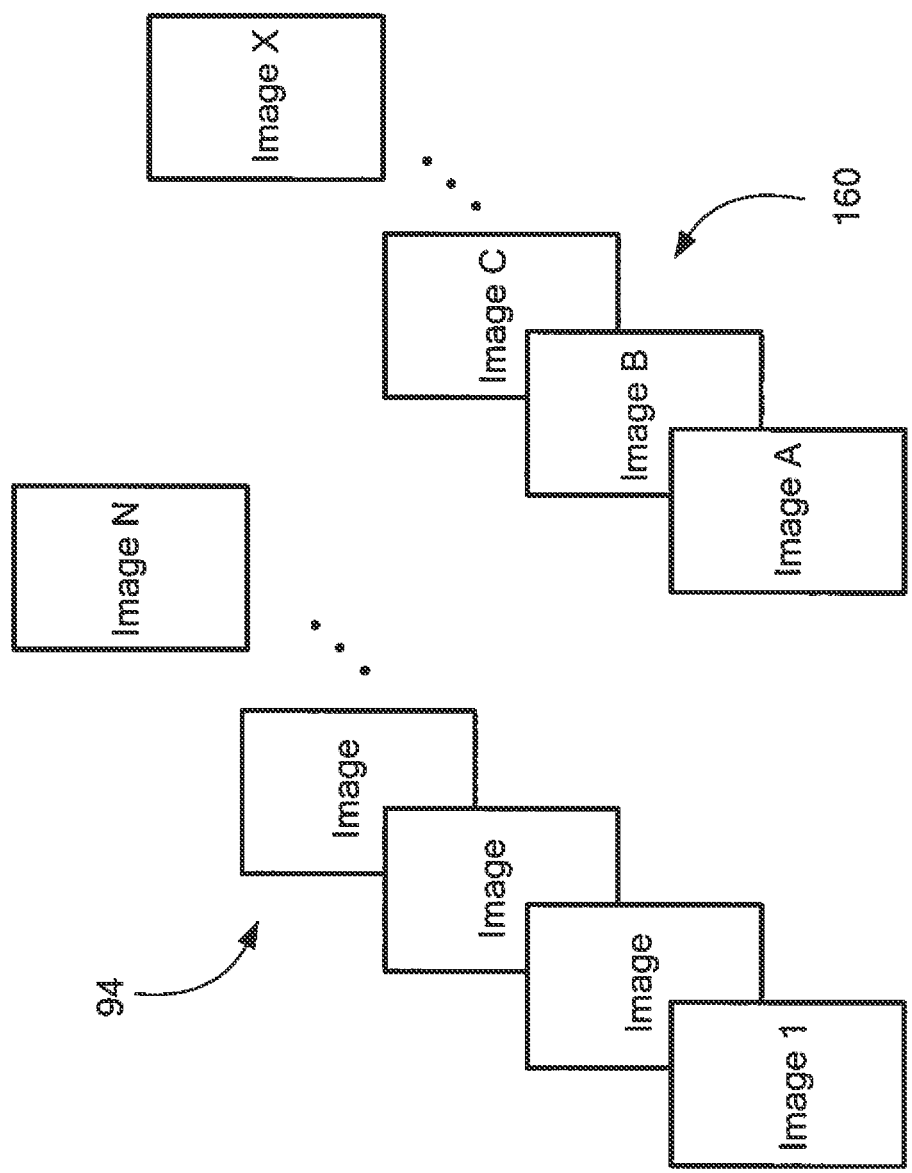
FIG. 7 depicts additional examples of time sequence of images shown in FIG. 3.

When discussed above with regard to step a) acquiring the time sequence of images 94, FIG. 3, in one design, the time sequence of images may be a subset of the time sequence of images 94 acquired in step a), e.g., time sequence of images 160, FIG. 7, Time sequence of images 160 does not necessarily need to start at the beginning of time sequence of images 94 or end at the end of time sequence of images 94. The time between each image in time sequence of images 160 does not necessarily need to equal the time between each image in time sequence of images 94. In one design, controller 70 discussed above may be configured to take a subset of the time sequence of images 94, e.g., time sequence of images 160. Such a subset need not necessarily start at the earliest point in time or end at the last point in time and controller 70 could also provide for re-sampling, e.g., take samples at lower frequencies and take samples at intermittent points in time e.g., the second first and third or any desired combination to create a time sequence of sequences. Controller 70 preferably reconstructs the non-contact PPG signal and based on the desired application and required processing time, controller 70 may resample (e.g., up sample or down sample) in order to meet the needs of the desired applications. This may be done by interpolation or similar techniques known to those skilled in the art.

Figure 8:
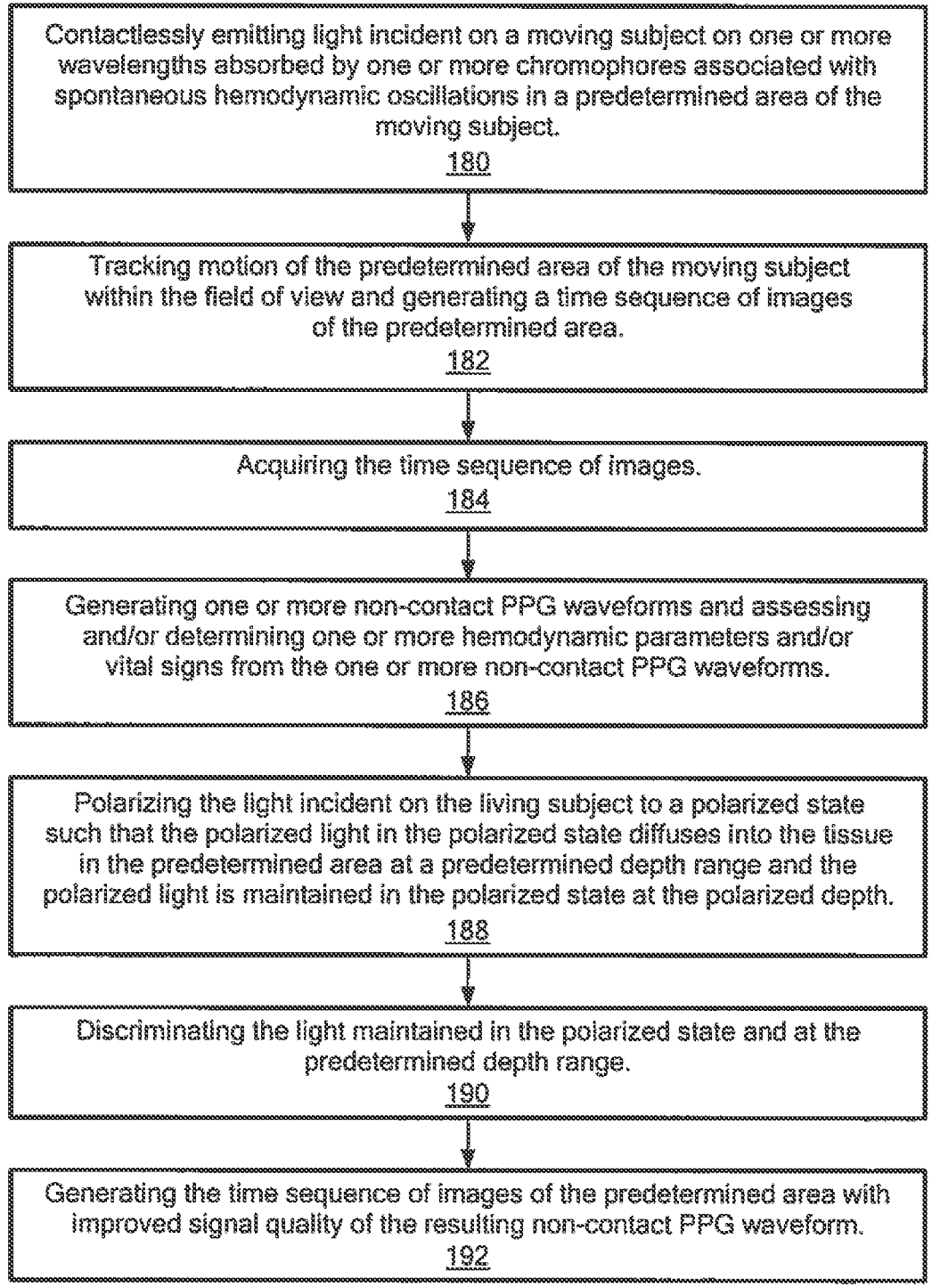
FIG. 8 is a block diagram showing one example of the primary steps of the method for contactlessly assessing and/or determining hemodynamic parameters and/or vital signs.

One embodiment of the method for assessing and/or determining hemodynamic parameters and/or vital signs includes contactlessly emitting light incident on a living subject at one or more wavelengths absorbed by one or more chromophores associated with spontaneous hemodynamic oscillations in a predetermined area of a living subject, step 180, FIG. 8. The method also includes tracking motion of the predetermined area of the living subject within a field of view and generating a time sequence of images of the predetermined area, step 182, acquiring the time sequence of images, step 184, and generating one or more non-contact PPG waveforms and assessing and/or determining one or more hemodynamic parameters and/or vital signs from the one or more non-contact PPG waveforms, step 186. The method also preferably includes polarizing the light incident on the living subject to a polarized state such that the polarized light in the polarized state diffuses into the tissue in the predetermined area at a predetermined depth range and the polarized light is maintained in the polarized state at the polarized depth, step 188, discriminating the light maintained in the polarized state and at the predetermined depth range, step 190, and generating the time sequence of images of the predetermined area with improved signal quality of the resulting non-contact PPG waveform, step 192.

Figure 9:
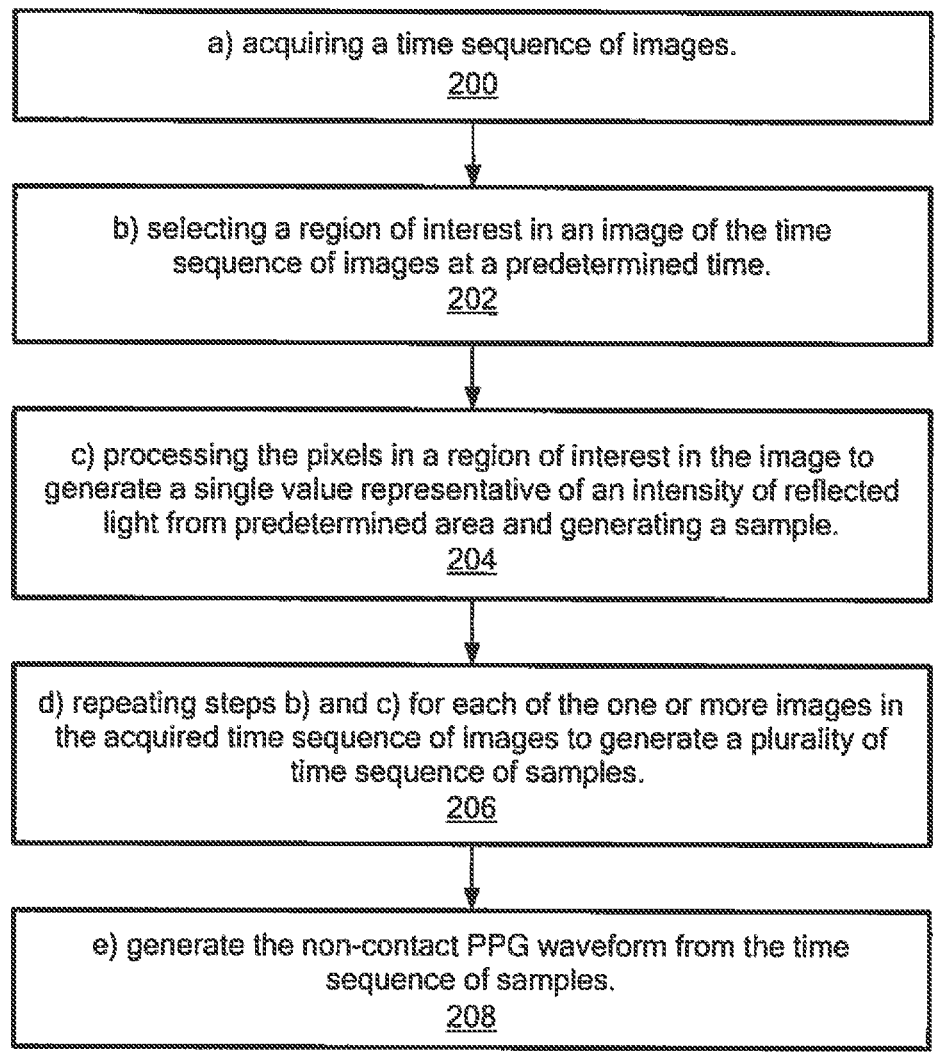

In one embodiment, the method may include acquiring a time sequence of images, step 200, FIG. 9. The method may also include selecting a region of interest in an image of the time sequence of images at a predetermined time, step 202. The method may also include processing the pixels in a region of interest in the image to generate a single value representative of an intensity of reflected light from the predetermined area and generating a sample, step 204. The method may also include repeating steps 202 and 204 for each of the one or more images in the acquired time sequence of images to generate a plurality of time sequenced samples, step 206. The method also includes generating the non-contact PPG waveform from the time sequence of samples, step 208.

The result is contactless system 10 and the method thereof accurately and effectively assesses and/or determines hemodynamic parameters and/or vital signs of a one or more moving living subjects without the need for any direct contact with one or more moving living subjects. Contactless system 10 and the method thereof may be used to assess and/or determine hemodynamic parameters and/or vital signs of a moving living subject or group of moving living subjects which may be located meters away from system 10, e.g., in a hospital, at an airport, a train station, a stadium, an airport, a gym, a room, or any type of facility where it may be desired to assess and/or determine hemodynamic parameters and/or vital signs of a large population of living subjects, Contactless system 10 and the method thereof is non-intrusive and may eliminate problems associated with conventional contact systems and methods to assess and/or determine hemodynamic parameters and/or vital signs that may result in skin irritation or interfere with the comfort of a moving living subject or a large group of moving living subjects. Contactless system 10 and the method thereof may also alleviate problems associated a moving living subject or a group of moving living subjects feeling anxious and/or nervous when sensors are placed in direct contact with their skin which may alter the heart rate and respiration and produce misleading results to healthcare providers or those who wish to monitor a subject or a group of subject's hemodynamic parameters and/or vital signs. Contactless system 10 and the method thereof also utilizes time domain analysis and does not rely on frequency domain analysis, reducing the effect of the noise on the quality of the RPPG estimation by replacing independent estimation with a joint estimation of different PPG waveforms of intensity of a skin at different regions of the skin, or using a complex two-dimensional hemodynamic map. Thus, system 10 and the method thereof may be less complex and cumbersome than the conventional systems and methods discussed in the Background section above.

For enablement purposes only, the following code portions arc provided which can be executed on one or more processors, a computing device, a computer, a smart device, or similar type device to early out the primary steps and/or functions of contactless system 10 for assessing and/or determining hemodynamic parameters an or vital signs discussed above with reference to one or more of FIGS. 1-9. Other equivalent algorithms and code can be designed by a software engineer and/or programmer skilled in the art using the information provided herein:

```
Define number Of Frames to be acquired;
Start up camera
Set up Camera specific acquisition parameters
Determine region of interest (mask)
Determine numberOfFrames to be acquired
%Acquire images and take average
for i = 1:numberOfFrames
    Individual Frame acquired from camera
    %Generate Sample and Save it
    intensity(i) = Takes mean of region of interest for each frame (i)
end
%Remove trend if any from non-contact PPG signal ( intensity(i) )
Identify polynomial coefficients to fit intensity(i)
with a polynomial curve
Remove trend from raw signal ( intensity(i) )
Retrieve vital signs
Identify main frequency components
Isolate Vital Signs
```

Figure 10:
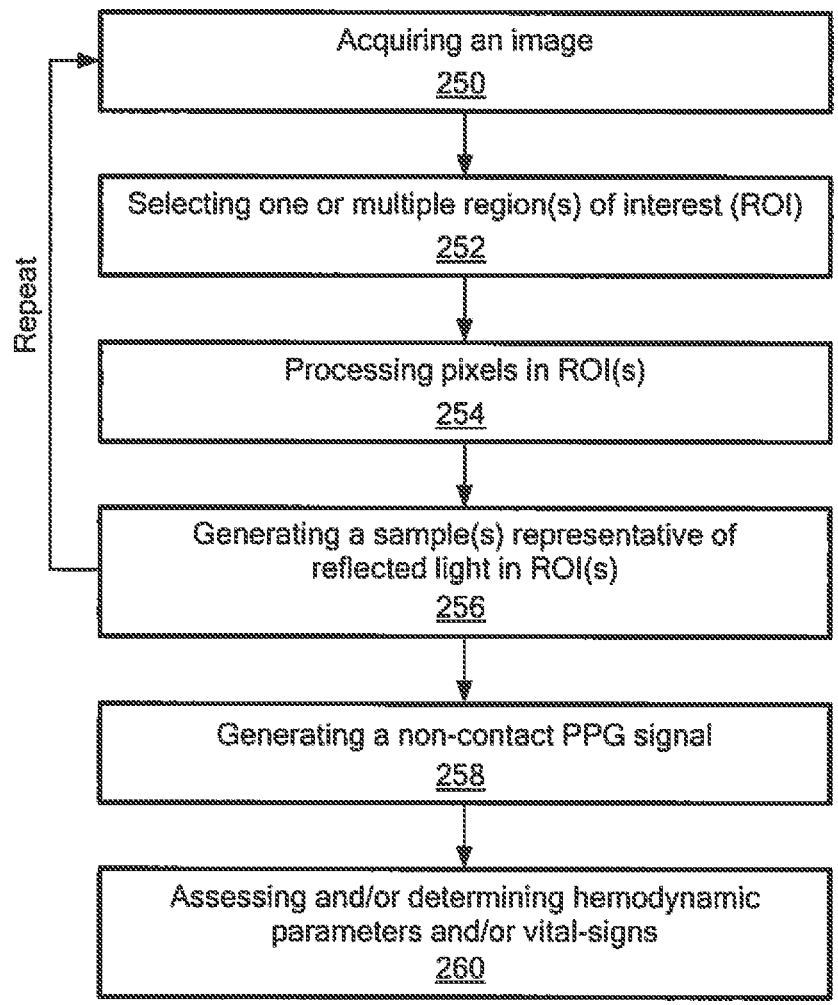
FIG. 10 is a flow chart showing one example of the primary steps for the system and method shown in one or more of FIGS. 1-9 to contactlessly assess and/or determine hemodynamic parameters and/or vital signs

In this example, the exemplary code above executed by processor 70 of system 10 and method thereof for contactlessly assessing and/or determining hemodynamic parameters and/or vital signs discussed above with reference to one or more of FIGS. 1-9, preferably includes acquiring an image, step 250, FIG. 10, selecting one or multiple region(s) of interest, step 252, processing pixels in the ROI(s), step 254, generating a sample(s) representative of reflected light in the ROI(s), step 256, generating a non-contact PPG signal, step 258, and accessing and/or determining hemodynamic parameters and/or vital signs, step 260.

As discussed above with reference to one or more FIGS. 1-10, system 10 and the method thereof includes camera subsystem 60 which receives reflected light from predetermined area 18 of moving living subject 16. In other examples, camera subsystem 60 may receive light that is transmitted through predetermined area 18 of moving living subject 16 and utilize one or more cameras which receive transmitted light from predetermined area 18 of moving living subject 16 to track motion of the predetermined area 18 of moving living subject 16 within a field of view of camera subsystem 60 and generate a time sequence of images of the predetermined area of the living subject, similar as discussed above.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may hear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A contactless system for at least one of assessing and determining at least one of hemodynamic parameters or vital signs, the system comprising:
one or more contactless light sources configured to emit light incident on a moving living subject;
a contactless camera subsystem comprising one or more cameras configured to receive reflected light from a predetermined area of the moving living subject and configured to follow and track the predetermined area when the living subject moves from one location to another location within a field of views of the camera subsystem and configured to generate a time sequence of images of the predetermined area of the living subject;
a controller coupled to the one or more contactless light sources and the camera subsystem configured to acquire the time sequence of images and configured to generate one or more non-contact photoplethysmography (PPG) waveforms using time domain analysis and to determine at least one of assessing or determining at least one of one or more hemodynamic parameters or vital signs from the one or more non-contact PPG waveforms;
one or more polarizers each coupled to one of the one or more contactless light sources and configured to polarize the emitted light to a polarized state such that the polarized light in the polarized state diffuses into tissue in the predetermined area at a predetermined depth range and the polarized light is maintained in the polarized state at the predetermined depth range; and
a detector polarizer coupled to each of the one or more cameras configured to discriminate the polarized light maintained in the polarized state and at the predetermined depth range from polarized light reflected from the tissue in the predetermined area which has not been maintained in the polarized state and at the predetermined depth range and configured to generate the time sequence of images of the predetermined area.

2. The system of claim 1 in which the controller is further configured to perform one or more of:
a) acquire the time sequence of images;
b) select a region of interest in an image of the time sequence of images at a predetermined point in time;
c) process the pixels in a region of interest in the image to generate a single value representative of an intensity of the reflected light from the predetermined area and generate a sample;
d) repeat steps b) and c) for one or more images in the acquired time sequence of images to generate a time sequence of samples; and
e) generate the non-contact PPG waveform from the time sequence of samples.

3. The system of claim 1 in which the one or more contactless light sources are configured to emit light having wavelengths in the visible, near infra-red or infra-red range.

4. The system of claim 1 in which the predetermined area of the living subject includes any area of the living subject having exposed skin.

5. The system of claim 1 in which the at least one of the one or more hemodynamic parameters or vital signs include one or more of: a heart rate, a resting heart rate, a heart rate variability, a respiration rate, and an oxygen saturation of the living subject.

6. The system of claim 1 in which the one or more cameras include one or more CCD cameras, one or more CMOS cameras, or one or more thermal imaging cameras.

7. The system of claim 1 in which the one or more cameras include an array of photodiodes or an array of phototransistors.

8. The system of claim 2 in which the region of interest is selected based on the intensity of the reflected light in each selected region across the time sequence of images.

9. The system of claim 2 in which the region of interest in each image is selected to correspond to a same portion of the predetermined area for each image of the sequence of images.

10. The system of claim 1 in which one or more of the cameras is configured to move relative to the living subject.

11. The system of claim 10 in which the one or more cameras is a moveable camera that is hand-held, body-worn, mounted on a drone, mounted on a wheeled dolly, mounted on a vehicle, or mounted on rails.

12. The system of claim 1 in which the field of view includes a composite field of view comprised of a field of view from two or more cameras, a wide field of view from a single camera, or one or more moving fields of view from one or more moving cameras.

13. A method for at least one of assessing and determining at least one of hemodynamic parameters and vital signs, the method comprising:
contactlessly emitting light incident on a living subject;
following and tracking a predetermined area when the living subject moves from one location to another location within one or more fields of view and generating a time sequence of images of the predetermined area;
acquiring the time sequence of images;
generating one or more non-contact photoplethysmography (PPG) using time domain analysis waveforms and determining at least one of assessing or determining at least one of one or more hemodynamic parameters or vital signs from the one or more non-contact PPG waveforms;
polarizing the light incident on the living subject to a polarized state such that the polarized light in the polarized state diffuses into tissue in the predetermined area at a predetermined depth range and the polarized light is maintained in the polarized state at the polarized depth;
discriminating the polarized light maintained in the polarized state and at the predetermined depth range from polarized light reflected from the tissue in the predetermined area which has not been maintained in the polarized state and at the predetermined depth range; and
generating the time sequence of images of the predetermined area.

14. The method of claim 13 further including performing one or more of:
a) acquiring a time sequence of images;
b) selecting a region of interest in an image of the time sequence of images at a predetermined time;
c) processing the pixels in a region of interest in the image to generate a single value representative of an intensity of reflected light from predetermined area and generating a sample;
d) repeating steps b) and c) for each one or more images in the acquired time sequence of images to generate a plurality of time sequence of samples; and
e) generating the non-contact PPG waveform from the time sequence of sample.

15. The method of claim 13 in which the light incident on the living subject is emitted having wavelengths in the visible, infrared, or infrared range.

16. The method of claim 13 in which the predetermined area of the living subject includes any area of the living subject having exposed skin.

17. The method of claim 13 in which at least one of the one or more hemodynamic parameters or vital signs include one or more of: a heart rate, a resting heart rate, a heart rate variability, a respiration rate, and an oxygen saturation of the living subject.

18. The method of claim 14 in which the region of interest is selected based on the intensity of the reflected light in each selected region across the time sequence of images.

19. The method of claim 18 in which the region of interest in each image is selected to correspond to a same portion of the predetermined area for each image of the sequence of images.

20. The method of claim 13 in which the tracking motion of the predetermined area of the living subject within the field of view is performed by a camera subsystem comprising one or more cameras configured to move relative to the living subject.

21. The method of claim 20 in which the one or more cameras is a moveable camera that is hand-held, body-worn, mounted on a drone, mounted on a wheeled dolly, mounted on a vehicle, or mounted on rails.

22. The method of claim 13 in which the field of view includes a composite field of view comprised of a field of view from two or more cameras, a wide field of view from a single camera, or one or more moving field of views from one or more moving cameras.

* * * * *